(12) United States Patent
Liu et al.

(10) Patent No.: US 7,544,668 B2
(45) Date of Patent: Jun. 9, 2009

(54) **SAPONINS DERIVED FROM *ILEX PUBESCENS* AND METHOD OF PURIFYING THE SAME**

(75) Inventors: Liang Liu, Hong Kong (CN); Jing Rong Wang, Hong Kong (CN); Hua Zhou, Hong Kong (CN); Zhi Hong Jiang, Hong Kong (CN)

(73) Assignee: Hong Kong Baptist University, Hong Kong SAR (CN)

( * ) Notice: Subject to any disclaimer, the term of this patent is extended or adjusted under 35 U.S.C. 154(b) by 69 days.

(21) Appl. No.: 11/560,849

(22) Filed: Nov. 17, 2006

(65) Prior Publication Data

US 2008/0119420 A1    May 22, 2008

(51) Int. Cl.
*A61K 31/7004* (2006.01)

(52) U.S. Cl. .............................. 514/33; 514/27; 514/25; 514/462; 424/736; 424/728

(58) Field of Classification Search ...................... 514/1
See application file for complete search history.

(56) References Cited

U.S. PATENT DOCUMENTS 4,987,125 A * 1/1991 Han et al. ..................... 514/33

* cited by examiner

*Primary Examiner*—Shengjun Wang
*Assistant Examiner*—Timothy E Betton
(74) *Attorney, Agent, or Firm*—Eagle IP Limited; Jacqueline C. Lui

(57) ABSTRACT

Two hitherto unreported novel triterpene saponins were isolated in substantially pure form from the root of *Ilex pubescens*. The chemical structures and some properties of the triterpene saponin fraction have been elucidated to possess anti-inflammatory and analgesic activity. These two novel triterpene saponins and the triterpene saponin fraction may be used as pharmaceutical compositions in humans and mammals in need of such treatment.

12 Claims, 9 Drawing Sheets

SAPONINS DERIVED FROM *ILEX PUBESCENS* AND METHOD OF PURIFYING THE SAME

FIELD OF INVENTION

The present invention is related to triterpene saponins. In particular, the present invention relates to triterpene saponins extracted from *Ilex Pubescens*.

BACKGROUND OF INVENTION

The dried root of the plant *Ilex pubescens* Hook. Et Arn. is known as "Mao-Dong-Qing" (毛冬青, MDQ) and is commonly used in traditional Chinese medicine for treatment of cardiovascular and inflammatory diseases. Previous chemical investigations reported that the roots and leaves of the plant contain simple phenolics, i.e. 3,4-dihydroxyacetophenone, hydroquinone, scopoletin, esculetin, homovanillic acid, vomifoliol and glaberide.

Pharmacological investigations demonstrated that extracts of MDQ could not only dilate blood vessels, but also improve micro-circulation, lower blood pressure, inhibit platelet aggregation, prevent thrombus, reduce cardiac ischemia, decline the excitation of the cardiac conduction system and enhance the ability of anoxia resistance of body.

Despite these publicly known activities, the anti-inflammatory and analgesic activities of *Ilex pubescens* extract have not been elucidated and may also be due to other hitherto unidentified compounds as well. It is therefore an object of the present invention to further isolate and identify biologically-active compounds from *Ilex pubescens*.

SUMMARY OF INVENTION

The present invention relates to a triterpene saponin fraction (named PSF) with anti-inflammatory and analgesic activities, and a pharmaceutical composition containing this fraction.

The present invention also relates to two substantially pure triterpene saponins pubescenoside C (PC) and pubescenoside D (PD) having the respective chemical formulae, and their pharmaceutically acceptable ester, amide, or prodrug thereof:

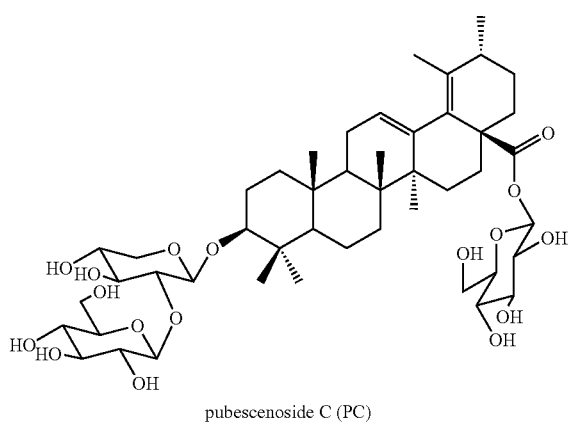

pubescenoside C (PC)

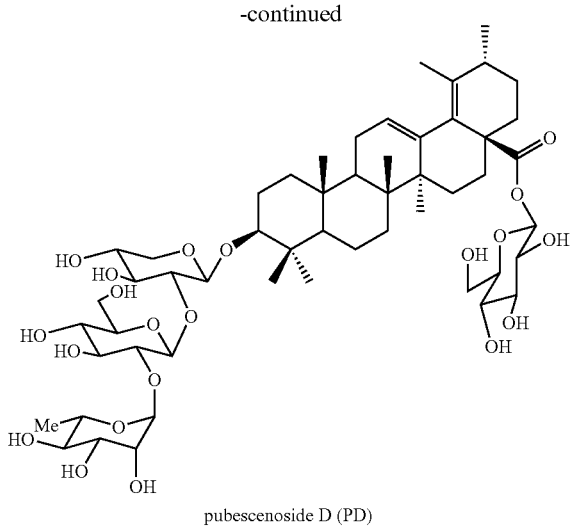

pubescenoside D (PD)

In another aspect, the present invention provides a method of preparing triterpene saponin fraction (PSF) from a plant material containing pubescenoside C or pubescenoside D, by mechanically reducing the plant material, extracting the reduced materials with a first solvent to form an extract, and purifying the triterpene saponins from the extract to a desired purity. The plant material can be, for example, the dried root of *Ilex pubescens*. The plant material can be mechanically reduced, for example, by chopping and grinding the plant material to powder. The first solvent can be methanol, and the extracting step can also involve the addition of water to the extract. The purifying step can involve, for example, partitioning the extract with ethyl acetate and n-butanol to obtain three fractions, subjecting the n-butanol fraction to hydrophobic interaction chromatography eluted with gradient methanol obtain a plurality of fractions, including the PSF. The PSF may be characterized by generating a fingerprint chromatogram showing 6 specific peaks using high performance liquid chromatography (HPLC) with evaporative light scattering detector (ELSD). Subsequently, the 6 peaks may be characterized by a range of ratio representing the relative concentration of each of the 6 compounds within the PSF.

In yet another aspect, the present invention provides a method of isolating pubescenoside C or pubescenoside D from a plant material, by subjecting the n-butanol fraction of MDQ extract to chromatography over a combination of Diaion HP-20, and Chromatorex ODS eluted by gradient methanol; subjecting the fractions eluted with 70% to 100% methanol to thin layer chromatography with $H_2SO_4$, and successively subjecting components thus visualized by the sulphuric acid to a further purification step. The purification step can also involve at least one of the following techniques: hydrophobic interaction chromatography, thin layer chromatography (TLC), and column chromatography.

Data provided below supports a biological use for PSF, PC and PD. Furthermore, the discovery and purification of PC and PD may also be used to provide diagnostic biomarkers for the standardisation of *Ilex pubescens* and quality control of its extracts. These purified markers may also be used for the detection and characterization of the PSF by properties such as presence, concentration, purity, and activity.

DETAILED DESCRIPTION OF THE PREFERRED EMBODIMENTS

Figure 1:
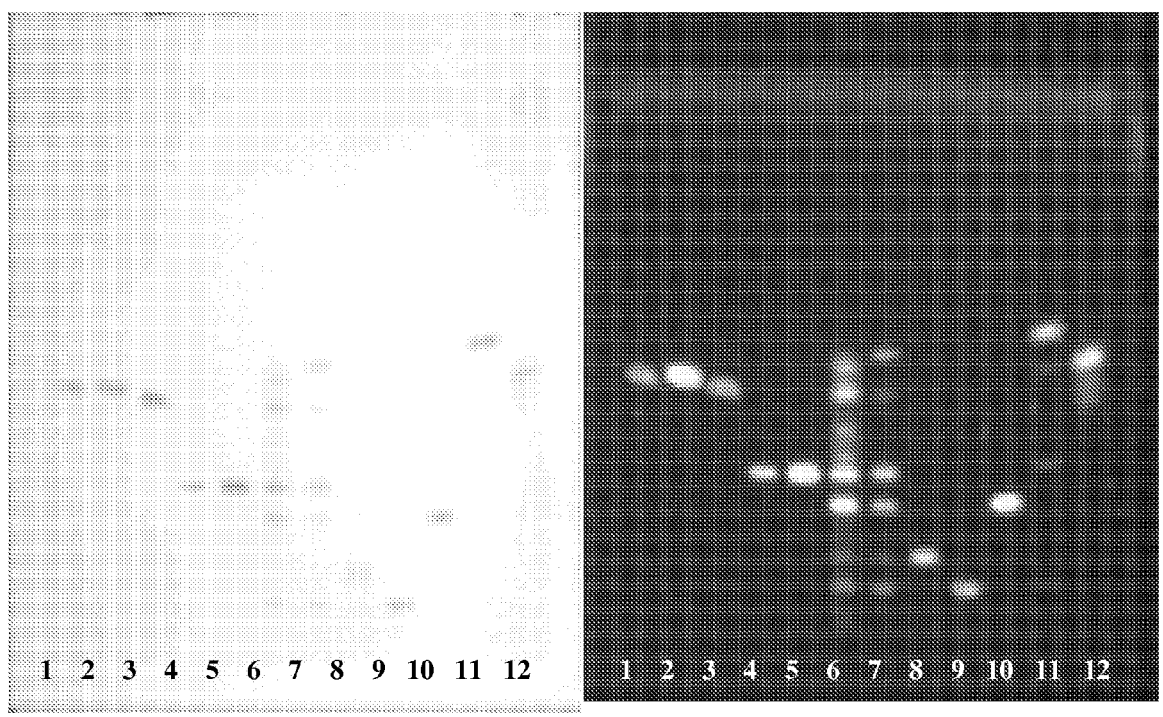
FIG. 1 shows the HPTLC analysis of the PSF.

As used herein, the term "ester" refers to a chemical moiety with formula —$(R)_n$—COOR', where R and R' are independently selected from the group consisting of alkyl, cycloalkyl, aryl, heteroaryl (bonded through a ring carbon) and heteroalicycylic (bonded through a ring carbon), and where n is 0 or 1.

An "amide" is a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicycylic (bonded through a ring carbon), and where n is 0 or 1. An amide may be an amino acid or a peptide molecule attached to a molecule of the present invention, thereby forming a prodrug.

Any amine, hydroxyl, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, $3^{rd}$ Edl, John Wiley & Sons, New York, .Y., 1999, which is incorporated herein in its entirety.

A "prodrug" refers to an agent that is converted into the parent drug in vivo. Prodrugs are often useful because, in some situation, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

As used herein and in the claims, the terms "comprise," "comprises," and "comprising" mean "including the following elements but not excluding others". For example, a method, apparatus, molecule or other item which contains A, B, and C may be accurately said to comprise A and B. Likewise, a method, apparatus, molecule or other item which "comprises A and B" may include any number of additional steps, components, atoms or other items as well.

Furthermore, "glu", "rha", and "xyl" are used herein as the abbreviations for the monosaccharides glucose, rhamnose, and xylose, respectively.

Also, unless otherwise defined, all technical and scientific terms used herein have the same meaning as commonly understood by one of ordinary skill in the art to which this invention belongs. Although any methods or materials similar to those described herein can be used in the practice or testing of the present invention, only the preferred embodiments are described. Utilizing the description below, a person skilled in the art of the preparation and use of Chinese herbal medicine can readily practice the methods of the present invention.

While dried material is traditionally used and preferred in Chinese herbal medicine, it must be recognized that drying of plant materials facilitates their storage, transportation and subsequent processing. Drying may not be a requirement to derive the benefits of these herbs. As such, it is understood that the present invention may be practiced with the corresponding quantity of the listed fresh plant materials as well. The use of fresh plant materials, sufficient to meet the requisite quantity and proportions of the extracts used, come under the scope of the present invention.

Also, while the root of *Ilex pubescens* is preferred as the plant part for use as it has the highest concentration of the compounds of interest, other parts of this plant may also be similarly used.

In this description, the term "substantially pure" as it refers to the isolation of the compounds of the present invention means a chemical purity of at least 75%, preferably 85-100%, more preferably 90-100% and most preferably 95-100%.

Plant Material. Dried root of *Ilex pubescens* was purchased from Cai-Zhi-Ling Chinese Herb Slice Co. Ltd., Guangzhou, Guangdong province, China.

General Experimental Equipments. $^1$H and $^{13}$C NMR data were recorded on a Varian 400 MHz FT-NMR Spectrometer (400 MHz for $^1$H and 100 MHz for $^{13}$C) NMR spectrometer. Coupling constants were given in Hz and chemical shifts were represented in δ (ppm). High performance liquid chromatograph (HPLC) was carried on an Agilent Series 1100 HPLC equipped with Agilent G1315A diode array detector (DAD) and Alltech Evaporative Light Scattering Detector (ELSD). Column chromatography was performed with Chromatorex ODS (100-200 mesh, Fuji Silysia Chemical Ltd.), $SiO_2$ (0.040~0.063 mm, Merck KgaA); TLC was performed on precoated Kieselgel 60 $F_{254}$ plate (0.2 mm thick, Merck KGaA) and the spots were detected by spraying with 10% sulfuric acid reagent.

Animal Material. Male and female ICR mice weighing 18-24 g and male SD rats weighing 150-210 g were purchased from the Laboratory Animal Services Center, the Chinese University of Hong Kong, Hong Kong. The animals were acclimated for more than 1 week under 12 hours light and 12 hours dark cycle at room temperature of 22±1° C. Chow diet and water were provided ad libitum. Animal care and treatment procedures conformed to the Institutional Guidelines and Animal Ordinance (Department of Health, Hong Kong Special Administrative Region.) Mice and rats were fasted for 16 hours and 48 hours, respectively, before experiment.

Mode of Administration. The PSF solutions for anti-inflammatory and analgesic experiments were prepared by dissolving the product in 30% propanediol solution (for i.p. injection) and 0.5% (w/v) carboxymethylcellulose sodium salt (CMC—Na) (for orally administration), respectively. The reference drug indomethacin for anti-inflammatory test was dissolved in a vehicle that consisted of 10% peanut oil, 10% Tween-80 and 80% distilled water. Rotundine was suspended in 0.5% (w/v) CMC—Na salt and used as reference drug for anti-nociceptive experiment.

Indomethacin, carrageenan, histamine, propanediol and Tween-80 were purchased from Sigma Chemical Co. (St. Louis, Mo., USA). Acetic acid (AR grade) was purchased from Uni-Chem (Hong Kong). Rotundine was purchased from Guangzhou Shiqiao Pharmaceutical Co. Ltd. (Guangzhou, China).

I. Preparation of PSF.

I.1. Methods.

The dried plant material (20 kg) was mechanically reduced, preferably to be powdered by chopping and grinding, and be extracted with methanol at room temperature for three times (160 L each time) to yield a total extract of 902 g. After the methanol is removed from the extract, the total extract was then suspended in water and then subjected to liquid-liquid partition. This is preferably done by successive addition of two solvents, ethyl acetate and n-butanol, to yield three fractions, i.e. EtOAc layer (240 g, discarded), $H_2O$ layer (253 g, discarded), and n-BuOH layer (409 g) which was further purified to produce PSF.

The n-BuOH layer was chromatographed over Diaion HP-20 eluted with gradient methanol ranging from 0% to 100% to obtain a plurality of fractions. The fractions eluted with 70% to 100% methanol were detected by silica gel high performance thin layer chromatography (HPTLC) [Mobile phase: $CHCl_3$-MeOH—$H_2O$ (8:2:0.2) or (7:3:0.5), spraying reagent: 10% sulfuric acid in ethanol]. Components visualized by sulfuric acid reagent (redish-purple spots appeared after visualizing) were combined to produce the said PSF. The HPTLC fingerprinting of PSF was conducted at a temperature of 22° C. and a humidity of 61%. The solvent front distance of 7.5 cm was used. The mobile phase was a mixture of chloroform:methanol:$H_2O$ (77.5:22.5:2.75). 10% sulfuric acid in ethanol was the spraying reagent used.

To obtain a HPLC-ELSD chromatogram of the PSF, 5 mg of PSF was dissolved in 1 ml MeOH to produce a test solution for HPLC fingerprint analysis. The HPLC fingerprint analysis was carried out on an Agilent 1100 series HPLC system. The separation was conducted on an Alltech Altima $C_{18}$ column (250 mm×4.6 mm, I.D.; particle size 5 μm) at room temperature. The mobile phase comprised water containing 0.4% formic acid (v/v, A) and acetonitrile containing 10% propan-2-ol (v/v, B). Elution was performed in the following order: 0-15 min, isocratic elution with A:B ratio of 65:35; 16-35 min, gradient elution with A:B ratio linearly changed from 65:35 to 30:70; 36-40 min, gradient elution with A:B ratio linearly changed from 30:70 to 0:100. Alltech Evaporative Light Scattering Detector (ELSD) 2000 (Tube temperature: 108.9° C., Gas flow rate: 2.9 mL/min) was employed for detection I.2. Results and Analysis.

FIG. 1 shows the HPTLC chromatogram of the PSF, visualized by 10% $H_2SO_4$/EtOH under visible light and $UV_{365}$ nm. Lane 1: unknown; Lane 2: unknown; Lane 3: *ilex*saponin A1; Lane 4: *ilex*saponin B2; Lane 5: pubescenoside C; Lane 6: PSF; Lane 7: mixed standards; Lane 8: pubescenoside D; Lane 9: chikusetsusaponin IVa; Lane 10: *ilex*saponin B3; Lane 11: unknown; Lane 12: *ilex*saponin B1. It can be seen that in lane 5 and lane 8, the bands corresponding to pubescenoside C and pubescenoside D show that both the purity and concentration of the two extracted triterpene saponins are high.

Figure 2:
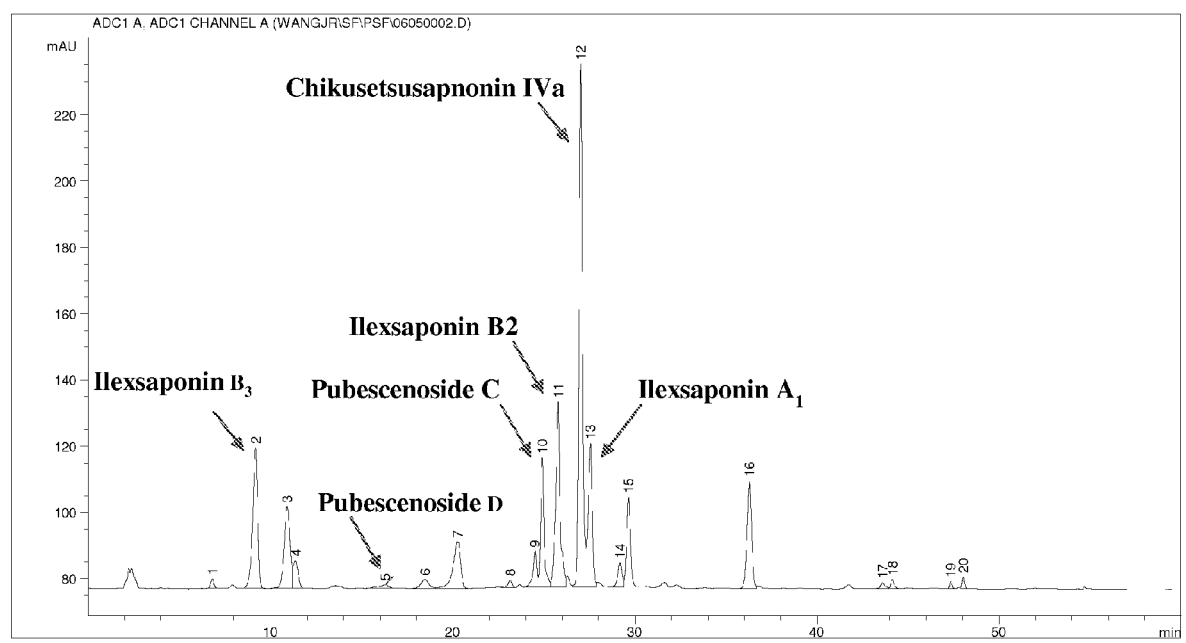
FIG. 2 shows the HPLC-ELSD fingerprint of the PSF, illustrating the 6 components with their retention time and relative concentration.
Figure 3:
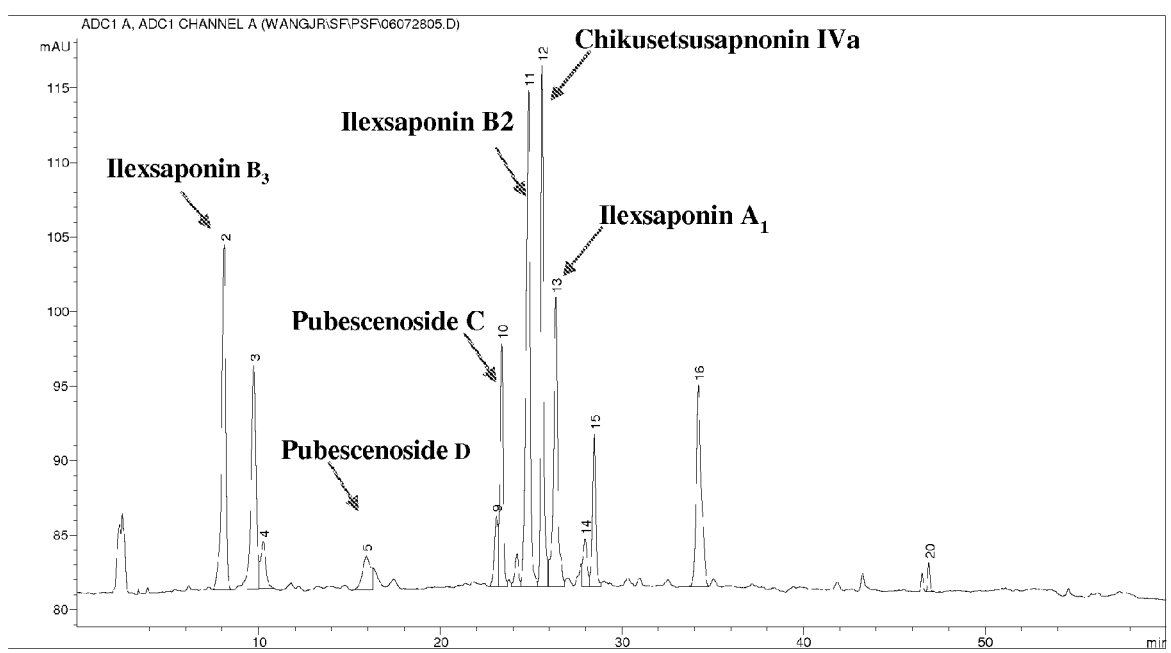
FIG. 3 shows a different HPLC-ELSD fingerprint of the PSF, illustrating the 6 components with their retention time and relative concentration, where a different lot of PSF from in FIG. 2 was used.

FIG. 2 and FIG. 3 (a repetition data) illustrate the HPLC-ELSD fingerprints compiled by the PSF, showing 6 components with their retention times and their relative concentrations. The data is tabulated in TABLE 1 and TABLE 2, respectively:

TABLE 1

| Peaks | Retention time (min) | Compound Name | Area percentage (%) FIG. 2 |
|---|---|---|---|
| 1 | 6.255 | unknown | 0.54 |
| 2 | 9.194 | Ilexsaponin $B_3$ | 10.23 |
| 3 | 10.924 | unknown | 7.28 |
| 4 | 11.375 | unknown | 1.93 |
| 5 | 16.293 | Pubescenoside D | 0.51 |
| 6 | 18.482 | unknown | 1.04 |
| 7 | 20.259 | unknown | 5.33 |
| 8 | 23.148 | unknown | 0.47 |
| 9 | 24.522 | unknown | 2.1 |
| 10 | 24.907 | Pubescenoside C | 6.45 |
| 11 | 25.786 | Ilexsaponin $B_2$ | 12.27 |
| 12 | 27.026 | Chikusetsusaponin IVa | 27.47 |
| 13 | 27.558 | Ilexsaponin $A_1$ | 8.75 |
| 14 | 29.181 | unknown | 1.54 |
| 15 | 29.651 | unknown | 5.09 |
| 16 | 36.294 | unknown | 7.48 |
| 17 | 43.598 | unknown | 0.39 |
| 18 | 44.139 | unknown | 0.45 |
| 19 | 47.349 | unknown | 0.24 |
| 20 | 48.031 | unknown | 0.44 |

TABLE 2

| Peaks | Retention time (min) | Compound Name | Area percentage (%) FIG. 3 |
|---|---|---|---|
| 1 | — | unknown | — |
| 2 | 8.116 | Ilexsaponin $B_3$ | 13.21 |
| 3 | 9.741 | unknown | 10.73 |
| 4 | 10.236 | unknown | 2.23 |
| 5 | 15.928 | Pubescenoside D | 2.69 |
| 6 | — | unknown | — |
| 7 | — | unknown | — |
| 8 | — | unknown | — |
| 9 | 23.095 | unknown | 2.35 |
| 10 | 23.292 | Pubescenoside C | 7.19 |
| 11 | 24.867 | Ilexsaponin $B_2$ | 18.66 |
| 12 | 25.603 | Chikusetsusaponin IVa | 13.53 |
| 13 | 26.363 | Ilexsaponin $A_1$ | 11.12 |
| 14 | 27.980 | unknown | 1.93 |
| 15 | 28.489 | unknown | 4.84 |
| 16 | 34.218 | unknown | 9.77 |
| 17 | — | unknown | — |
| 18 | — | unknown | — |
| 19 | — | unknown | — |
| 20 | 46.913 | unknown | 0.60 |

In another embodiment of the present presentation, the data of TABLE 1 and TABLE 2 is simplified by omitting the peaks corresponding to unknown compounds. The remaining 6 compounds of the PSF are described in TABLE 3 by their retention times and area ratios as compared to the total concentration to the PSF. The area ratio is obtained by dividing the area of each of the 6 component peaks by the total area covered by all of the 6 component peaks.

TABLE 3

| Peaks | Retention time (min) (FIG. 2, FIG. 3) | Compound Name | Area percentage (%) FIG. 2 | FIG. 3 | Area ratio range |
|---|---|---|---|---|---|
| 2 | 9.194, 8.116 | Ilexsaponin $B_3$ | 10.23 | 13.21 | 16%–20% |
| 5 | 16.293, 15.928 | Pubescenoside D | 0.51 | 2.69 | 1%–4% |
| 10 | 24.907, 23.292 | Pubescenoside C | 6.45 | 7.19 | 10%–19% |
| 11 | 25.786, 24.867 | Ilexsaponin $B_2$ | 12.27 | 18.66 | 18%–28% |
| 12 | 27.026, 25.603 | Chikusetsusaponin IVa | 27.47 | 13.53 | 20%–42% |
| 13 | 27.558, 26.363 | Ilexsaponin $A_1$ | 8.75 | 11.12 | 13%–17% |

The above tabulated data was compiled using different batches of the PSF.

II. Isolation of Pubescenoside C and Pubescenoside D

II.1. Methods.

PSF (10 g) was subjected to column chromatography over octadecyl silane (ODS) [The weight of ODS: 1.5 kg; Mobile phase: gradient methanol ranging from 50% to 100% (v/v, increase at 5% percentage, 1.5 L for each gradient)]. The $3^{rd}$ fraction (2.1 g, eluted with 70% methanol), $4^{th}$ fraction (1.65 g, eluted with 70% to 75% methanol), $5^{th}$ fraction (2.32 g, eluted with 75% methanol) and $6^{th}$ fraction (3.0 g, eluted with 80% methanol) were further subjected to chromatography over silica gel [The weight of $SiO_2$: 50 to 70 times of sample weight; Mobile phase: $CHCl_3$-MeOH—$H_2O$ (9:1:0.1); (8:2:0.2); (7:3:0.5); 200 to 300 ml mobile phase of each gradient; Flowrate was approximately 8 ml/min] respectively to yield 6 compounds. Among them, compound 1 [isolated from $6^{th}$ fraction and eluted with $CHCl_3$-MeOH—$H_2O$ (8:2:0.2) over $SiO_2$ column chromatography] and compound 2 (isolated from 6th fraction, eluted with $CHCl_3$-MeOH—$H_2O$ (7:3:0.5) over $SiO_2$ column chromatography) were newly isolated triterpene saponins and were named as pubescenoside C and pubescenoside D respectively.

II.2. Results and Analysis.

Pubescenoside C was isolated as an amorphous powder and showed positive reaction to $H_2SO_4$ reagent in thin-layer chromatography. High resolution positive ISE-TOF gave an $[M+Na]^+$ ion peak at m/z 933.4878, indicating its molecular formula to be $C_{47}H_{74}O_{17}$. The ESI-MS (negative ion mode) of Pubescenoside C gave an $[M-H]^-$ ion peak at m/z 909.6; $[M-H-Glc]^-$ at 747.4, $[M-H-Glc-Glc]^-$ at 585.4, and $[M-H Glc-Glc-130]^-$ at 455.4, indicating the presence of the moieties of two glucose and one xylose. On the basis of the results of $^1H$ and $^{13}C$ NMR data illustrated in (TABLE 4, 5), the structure of pubescenoside C was established as 3-O-β-D-glucopyranosyl (1→2)-β-D-xylopyranosyl-urs-12,18-dien-28-oic acid 28-O-β-D-glucopyranosyl ester.

TABLE 4

$^1$H NMR data of saponins Pubescenoside C and Pubescenoside D

| H | Pubescenoside C (PC) | Pubescenoside D (PD) |
|---|---|---|
| $CH_3$ | 0.87(3H, s) | 0.85(1H, s) |
|  | 1.09(6H, s) | 1.10(3H, s) |
|  | 1.13(3H, s) | 1.13(6H, s) |
|  | 1.29(3H, s) | 1.36(3H, s) |
|  | 1.78(3H, s) | 1.84(3H, s) |
| 30-$CH_3$ | 1.02(3H, d, J=7.2Hz) | 1.02(3H, d, J=7.2Hz) |
| 3-H | 3.32(1H, dd, J=5, 12Hz) | 3.35(1H, dd, J=5, 12Hz) |
| 12-H | 5.60(1H, m) | 5.60(1H, m) |
| Xyl-1 | 4.89(1H, d, J=6Hz) | 4.94(1H, d, J=6Hz) |
| Glc-1 | 5.40(1H, d, J=7.8Hz) | 5.83(1H, d, J=7.8Hz) |
| Rha-1 | — | 6.45(1H, s) |
| Rha-6 | — | 1.83(1H, d, J=6.4Hz) |
| 28-O-Glc-1 | 6.34(1H, d, J=8Hz) | 6.35(1H, d, J=8Hz) |

TABLE 5

$^{13}$C NMR data of Pubescenoside C and Pubescenoside D

| Aglycone | PC | PD | Sugar moiety | PC | PD |
|---|---|---|---|---|---|
| C-1 | 39.6 | 39.9 | 3-O-sugar |  |  |
| C-2 | 27.3 | 27.2 | xyl-1 | 106.5 | 106.2 |
| C-3 | 89.0 | 90.0 | xyl-2 | 83.2 | 79.4 |
| C-4 | 39.8 | 40.3 | xyl-3 | 78.1 | 78.2 |
| C-5 | 56.3 | 56.7 | xyl-4 | 71.7 | 71.5 |
| C-6 | 18.5 | 18.9 | xyl-5 | 66.8 | 66.9 |
| C-7 | 35.0 | 35.4 | Glc-1 | 106.4 | 102.4 |
| C-8 | 39.8 | 39.9 | Glc-2 | 77.2 | 79.7 |
| C-9 | 48.4 | 48.7 | Glc-3 | 78.6 | 79.2 |
| C-10 | 37.0 | 37.4 | Glc-4 | 71.3 | 72.6 |
| C-11 | 23.8 | 24.1 | Glc-5 | 78.2 | 79.1 |
| C-12 | 127.4 | 127.4 | Glc-6 | 62.7 | 63.6 |
| C-13 | 139.1 | 139.2 | Rha-1 |  | 102.3 |
| C-14 | 44.9 | 45.2 | Rha-2 |  | 72.8 |
| C-15 | 29.3 | 29.4 | Rha-3 |  | 72.8 |
| C-16 | 26.5 | 26.8 | Rha-4 |  | 74.6 |
| C-17 | 50.7 | 50.2 | Rha-5 |  | 69.7 |
| C-18 | 135.0 | 135.1 | Rha-6 |  | 18.8 |
| C-19 | 136.0 | 136.0 | 28-O-sugar |  |  |
| C-20 | 34.7 | 35.4 | Glc-1 | 96.3 | 96.0 |
| C-21 | 30.9 | 29.0 | Glc-2 | 74.3 | 74.4 |
| C-22 | 35.0 | 35.4 | Glc-3 | 79.1 | 79.5 |
| C-23 | 29.0 | 29.0 | Glc-4 | 71.4 | 71.4 |
| C-24 | 17.0 | 17.4 | Glc-5 | 78.6 | 79.1 |
| C-25 | 16.5 | 16.7 | Glc-6 | 62.4 | 624 |
| C-26 | 18.5 | 19.6 |  |  |  |
| C-27 | 22.5 | 22.8 |  |  |  |
| C-28 | 175.5 | 175.5 |  |  |  |
| C-29 | 20.4 | 20.8 |  |  |  |
| C-30 | 20.6 | 21.0 |  |  |  |

Pubescenoside D (Compound 2) was also isolated as an amorphous powder and showed positive reaction to $H_2SO_4$ reagent in thin-layer chromatography. High resolution positive ESI-Q-TOF gave an $[M+Na]^+$ ion peak at m/z 1079.5419, indicating its molecular formula to be $C_{53}H_{84}O_{21}$. The ESI-Q-TOF mass spectrum (negative ion mode) of Pubescenoside D gave an $[M-H]^-$ ion peak at m/z 1055.6; and $[M-Glc]^-$ at 893.4, indicating the presence of the moieties of two glucose, one xylose and one rhamnose. On the basis of the results of $^1H$ and $^{13}C$ NMR data illustrated in (TABLE 4, 5), the structure of pubescenoside D was established as 3-O-α-L-rhamnopyranosyl(1→2)-β-D-glucopyranosyl(1→2)-β-D-xylopyranosyl-urs-12,18-dien-28-oic acid 28-O-β-D-glucopyranosyl ester.

Figure 4:
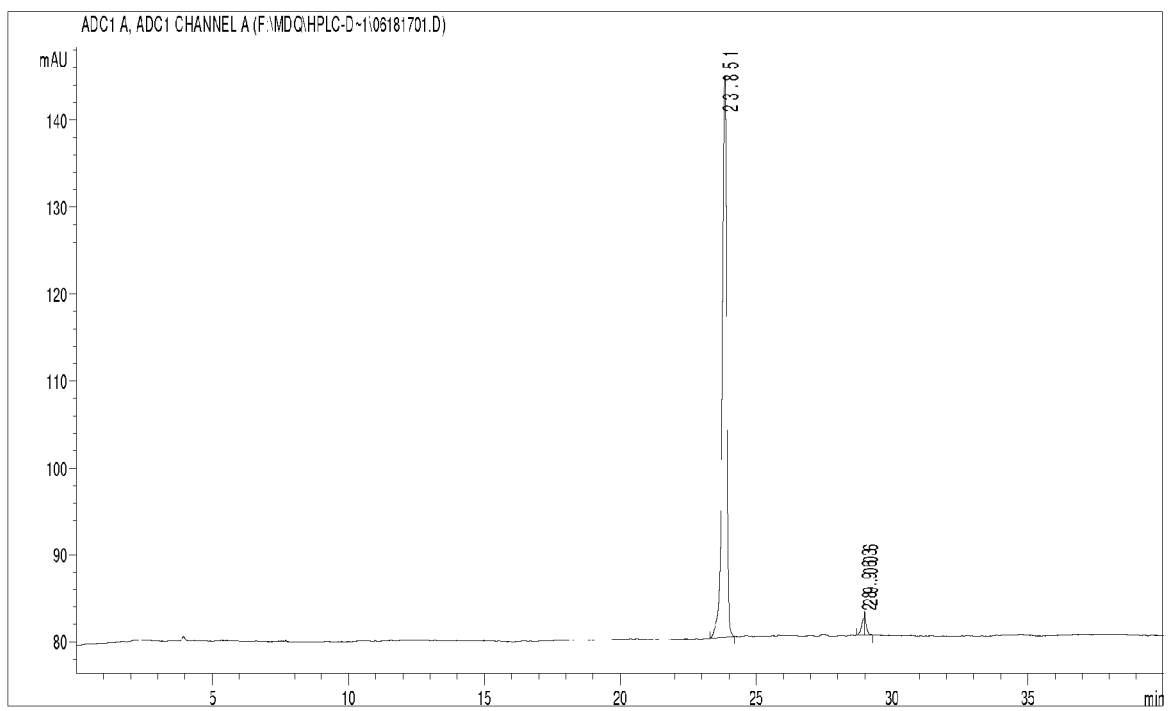
FIG. 4 shows the HPLC-ELSD chromatogram showing the purity of pubescenoside C.
Figure 5:
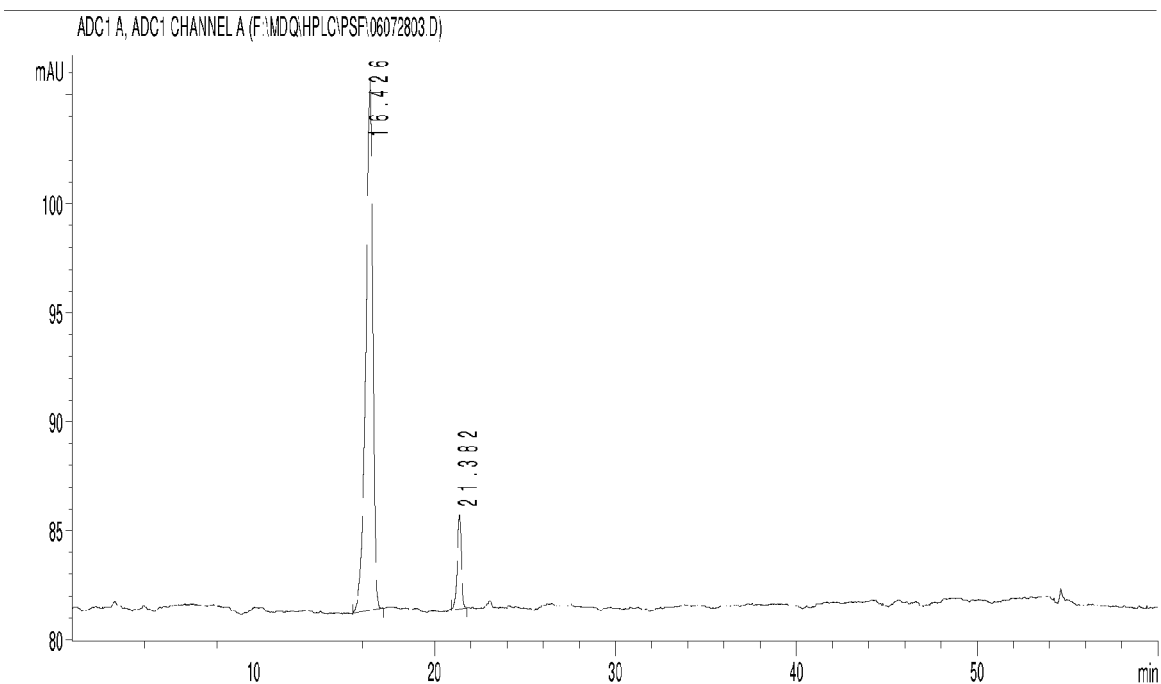
FIG. 5 shows the HPLC-ELSD chromatogram showing the purity of pubescenoside D.

The purities of the pubescenoside C and pubescenoside D were determined by high pressure liquid chromatography (HPLC) with evaporative light scattering detector (ELSD). The method is described below. The HPLC-ELSD chromatograms showing the purities of pubescenoside C and pubescenoside D are presented in FIGS. 4 and 5, respectively. It was determined that the purities of the pubescenosides C and D to be 97.1% and 90.6%, respectively.

III. Biological Activity of Pubescenoside C and Pubescenoside D

III.1. Induction of Acute Inflammation in Rat Hind Paws by Carrageenan.

III.1a. Methods

In a separate embodiment, the present invention provides a method to determine the anti-inflammatory effect of the PSF comprising pubescenoside C and pubescenoside D, by examining the PSF with carrageenan induced paw edema in rats.

The experiment was conducted as previously described by Winter[1]. At the induction, each rat was injected with 0.1 ml freshly prepared carrageenan (1% w/v) in physiological saline (0.9% w/v NaCl) into subplantar tissues of the right hind paw. The left hind paws without injection were used as controls. PSF was i.p. administrated 10 minutes prior to carrageenan injection. Control animals received an appropriate volume of 30% propanediol. Indomethacin was orally administrated 1 hr before the carrageenan injection as a reference drug.

The volumes (ml) of both hind paws were measured using a plethysmometer (Plethysmometer 7150, UGO Basile, Italy) at 1 hour before the induction and 1, 2, 3, 4, 6, and 8 hours after the induction. The increased volumes (paw edema) of the right hind paws of rats were calculated by the following equation: the increased rate (%)=(B−A)/A×100, where A and B represent the paw volumes before and at different time points after the induction, respectively.

III.1b. Results and Analysis.

Figure 6:
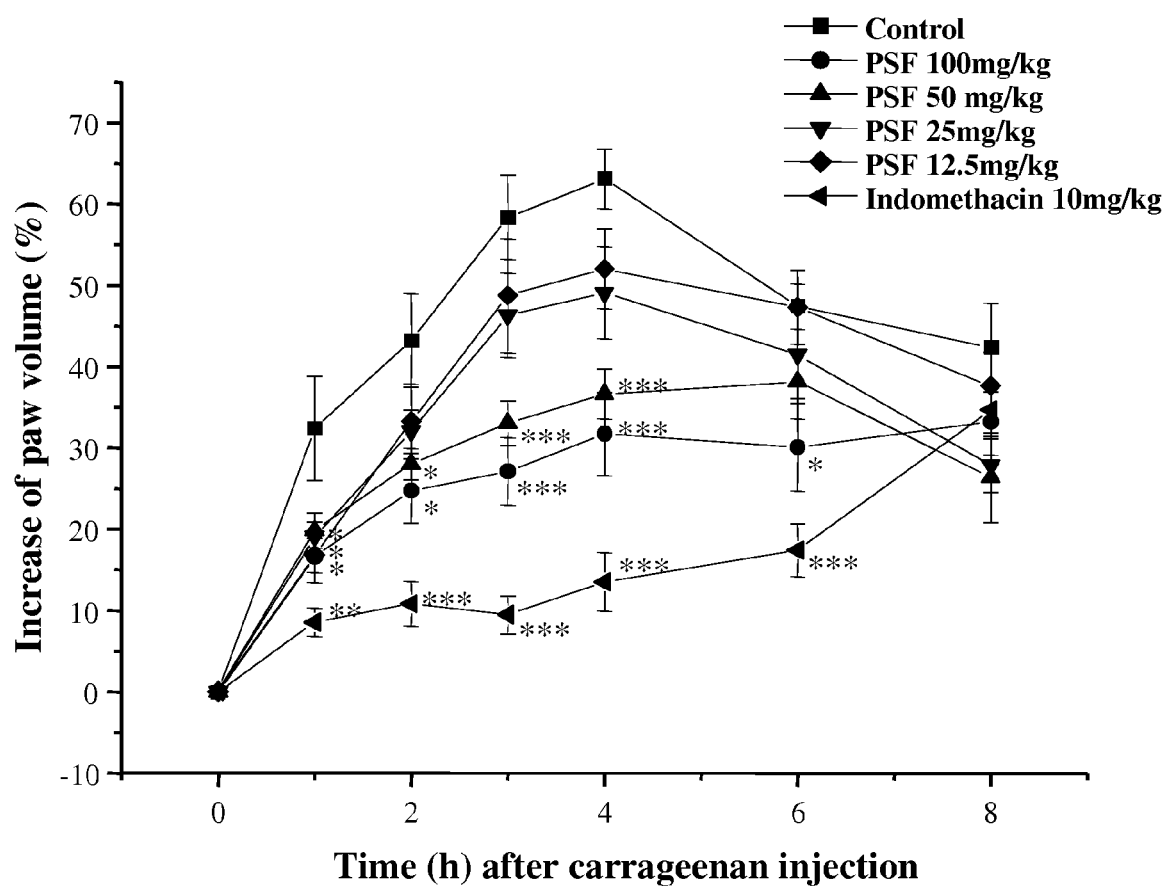
FIG. 6 shows the inhibition of carrageenan-induced paw edema of rats by treatment of different doses of PSF, indomethacin or solvent.

Illustrated in FIG. 6 and TABLE 6, measurement was conducted at 1, 2, 3, 4, 6 and 8 hours after injection of carrageenan. It can be seen that the PSF showed significant inhibiting effect on carrageenan-induced paw edema in rats in a dose-dependent manner. The maximum phlogistic response of carrageenan was observed at 3-4 hours after the injection in the animals of control group. Data from PSF treated animals with the doses of 50 mg/kg and 200 mg/kg at 1, 2, 3, 4, 6 hours after carrageenan injection showed significant differences in comparison with the data of the vehicle-treated animals at the same time points, while the animals treated with doses of 25 mg/kg and 12.5 mg/kg only showed significant differences at 1 hour.

TABLE 6

| Groups | Dosages (mg/kg) | Changes in swelling percentage after carrageenan injection (%) | | | | | |
| --- | --- | --- | --- | --- | --- | --- | --- |
| | | 1 h | 2 h | 3 h | 4 h | 6 h | 8 h |
| Control | — | 32.44 ± 18.15 | 43.24 ± 16.20 | 58.34 ± 14.62 | 63.10 ± 10.29 | 47.40 ± 7.83 | 42.38 ± 15.35 |
| PSF | 100 | 16.63 ± 10.23* | 24.75 ± 12.62* | 27.13 ± 13.13*** | 31.73 ± 16.21*** | 30.09 ± 17.17* | 33.23 ± 13.02 |
| PSF | 50 | 19.85 ± 6.83 | 28.02 ± 6.01* | 33.08 ± 8.68*** | 36.64 ± 9.79*** | 38.15 ± 14.61 | 26.36 ± 17.43 |
| PSF | 25 | 19.12 ± 5.70* | 32.04 ± 8.39 | 46.30 ± 16.39 | 49.10 ± 17.97 | 41.47 ± 16.84 | 27.85 ± 13.02 |
| PSF | 12.5 | 16.81 ± 6.05* | 33.28 ± 12.97 | 48.74 ± 19.83 | 52.02 ± 13.83 | 47.30 ± 12.79 | 37.63 ± 11.89 |
| Indomethacin | 10 | 8.54 ± 4.97** | 10.80 ± 7.77*** | 9.49 ± 6.63*** | 13.53 ± 10.13*** | 17.43 ± 9.21*** | 34.70 ± 9.21 |

Each data represents the mean ± S.D. of 8-10 rats.
***= $P < 0.001$;
**= $P < 0.01$;
*= $P < 0.05$, compared with the control group at the same time point.

III.2. Induction of Acute Inflammation in Rat Hind Paws by Histamine.

III.2a. Methods.

In another embodiment, the present invention provides another method to determine the anti-inflammatory effect of the PSF comprising pubescenoside C and pubescenoside D, by examining the PSF with histamine induced paw edema in rats.

The acute inflammation in the hind paws was induced by the subcutaneous injection of 0.05 ml 1% prepared solutions of histamine into right hind paws of rats. The left hind paws were used as controls. Administration of PSF (12.5 mg/kg, 25 mg/kg, 50 mg/kg, 100 mg/kg body weight, i.p. injection), or of the vehicle (30% propanediol) was performed at 10 minutes prior to carrageenan injection. Indomethacin was orally administrated at 1 hour before the induction. The volumes of the injected and control paws were measured at different time points designed from 0.5 to 4 hours after injection of histamine. The increased rates in paw volume were calculated in the same way as in carrageenan.

III.2b. Results and Analysis.

Figure 7:
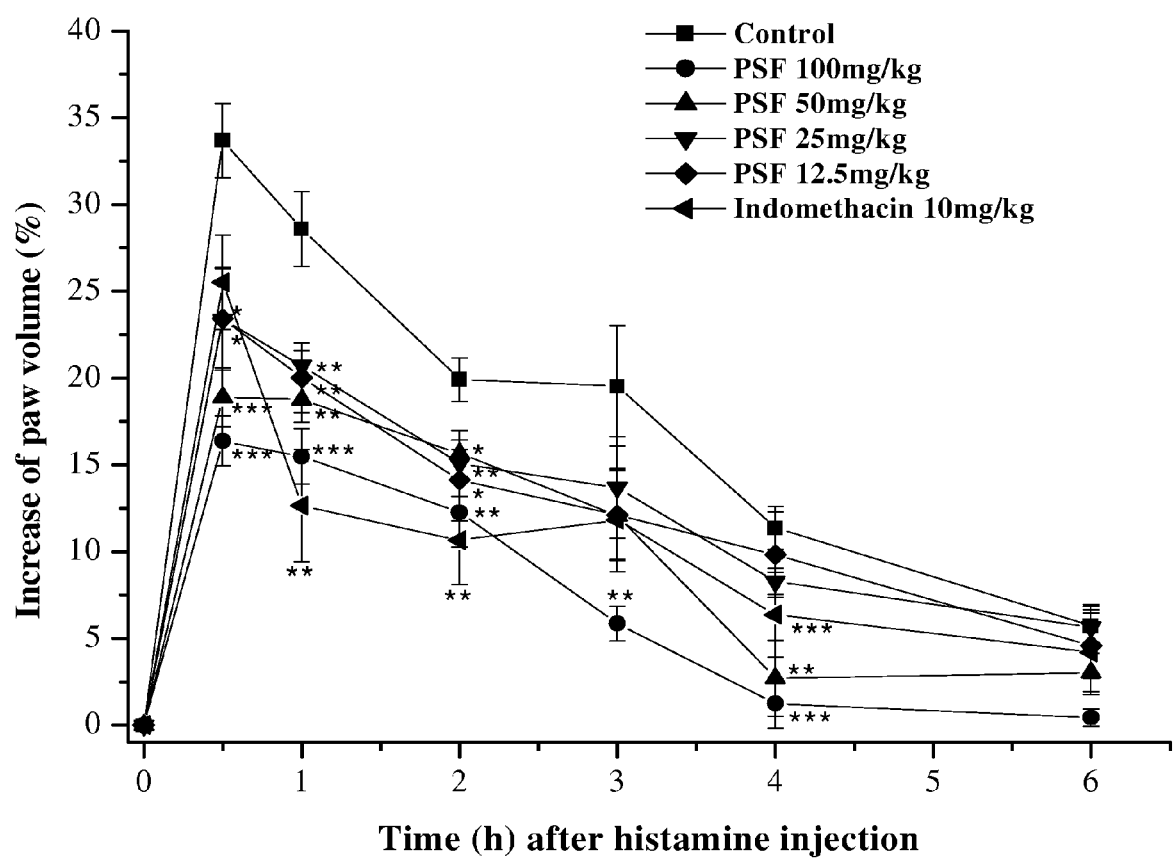
FIG. 7 shows the inhibition of histamine-induced paw edema of rats by treatment of different doses of PSF, indomethacin or solvent.

Illustrated in FIG. 7 and TABLE 7, measurement was conducted at 0.5, 1, 2, 3, 4 and 6 hours after the injection of histamine. Significant edema with a peak at 1 hour and with rapid decrease from 2 hours after injection was observed. All four doses (100, 50, 25 and 12.5 mg/kg) of PSF significantly inhibited edema within 2 hours after the induction. Indomethacin (10 mg/kg) showed significant inhibitory effect exhibiting at a later time than that of PSF. These results demonstrated that the PSF showed significant inhibiting effect on histamine-induced paw edema in rats in a dose-dependent manner.

TABLE 7

| Groups | Dosages (mg/kg) | Changes in swelling percentage after Carrageenan injection (%) | | | | | |
|---|---|---|---|---|---|---|---|
| | | 0.5 h | 1 h | 2 h | 3 h | 4 h | 6 h |
| Control | | 33.68 ± 6.03 | 28.58 ± 6.12 | 19.92 ± 3.61 | 19.54 ± 9.84 | 11.36 ± 3.44 | 5.72 ± 3.39 |
| PSF | 100 | 16.03 ± 5.12*** | 15.13 ± 5.21*** | 11.92 ± 6.61** | 5.49 ± 3.66** | 0.92 ± 4.54*** | 0.43 ± 1.66 |
| PSF | 50 | 18.90 ± 5.31*** | 18.76 ± 4.15** | 15.66 ± 4.17* | 12.07 ± 8.21 | 2.71 ± 6.93** | 3.03 ± 3.57 |
| PSF | 25 | 23.38 ± 9.18* | 20.72 ± 2.65** | 15.08 ± 2.48** | 13.68 ± 9.23 | 8.27 ± 2.36 | 5.64 ± 3.43 |
| PSF | 12.5 | 23.42 ± 8.35* | 20.02 ± 5.68** | 14.12 ± 6.62* | 12.12 ± 7.32 | 9.83 ± 7.00 | 4.59 ± 5.29 |
| Indomethacin | 10 | 29.72 ± 10.67 | 14.64 ± 9.21** | 11.51 ± 6.61** | 11.35 ± 7.35 | 7.43 ± 6.05*** | 4.17 ± 6.05 |

Each data represents the mean ± S.D. of 8-9 rats.
*** = $P < 0.001$;
** = $P < 0.01$;
* = $P < 0.05$, compared with the control group at the same time point III.3. Visceral Nociceptive Model Induced by Acetic Acid Stimulation in Mice.

III3a. Methods

In a further embodiment, the present invention provides a method to determine the analgesic effect of the PSF comprising pubescenoside C and pubescenoside D, by examining the PSF with the abdominal writhing test involving the peritoneal injection of acetic acid in mice.

The abdominal writhing test induced by chemical stimulation of acetic acid was performed in mice as originally described by Siegmund[2]. Briefly, PSF (200, 100, 50 mg/kg body weight) and vehicle (0.5% CMC—Na) were orally administrated 30 minutes prior to acetic acid injection. Rotundine was orally administrated 1 hour before acetic acid injection. After intraperitoneal injection of 0.2 ml acetic acid (0.8% w/v) in physiological saline (0.9% w/v NaCl), animals were isolated for observation. The numbers of abdominal writhing syndrome/events, which consisted of the contraction of the abdominal area with extension of hind legs, were recorded during a 15 minutes period in each animal.

III.3a. Results and Analysis.

Figure 8:
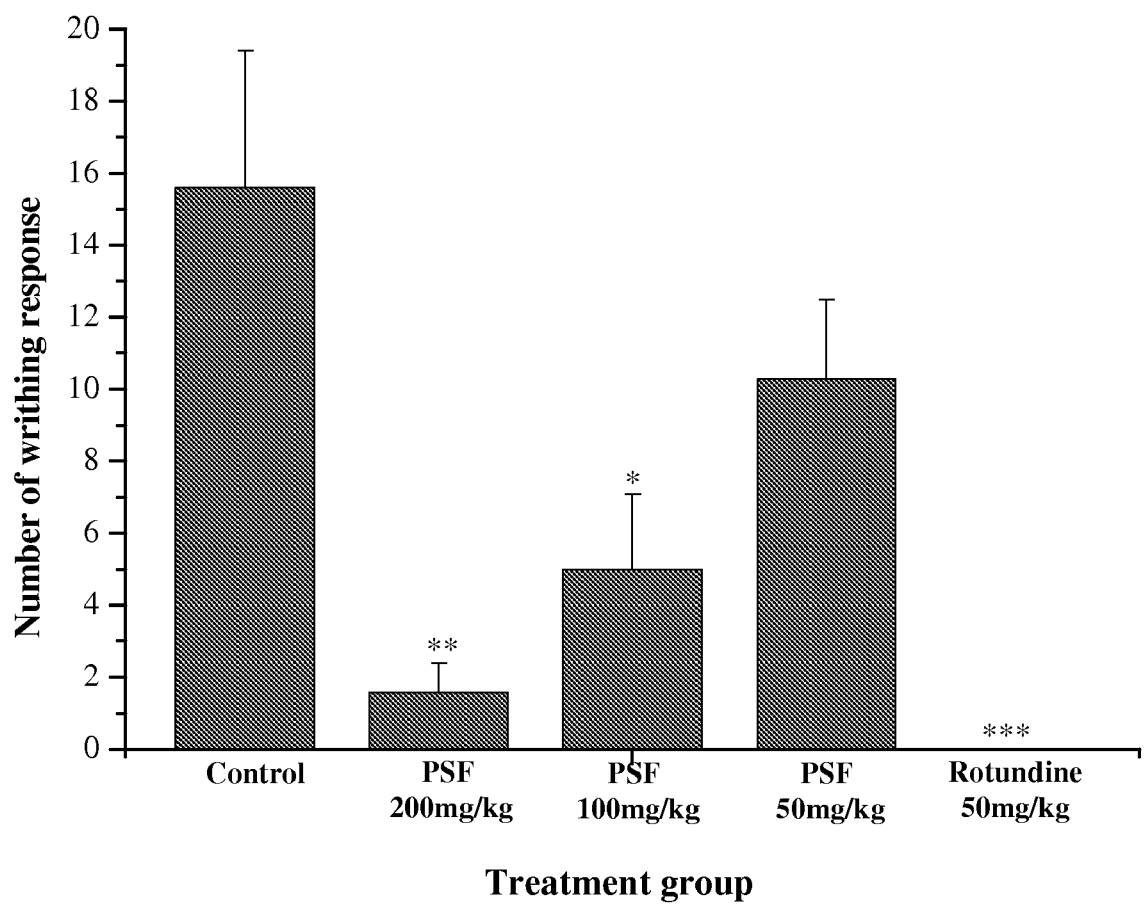
FIG. 8 shows analgesic effect of PSF at different dosages on acetic acid induced writhing response of mice.

From the data illustrated in FIG. 8 and TABLE 8, it can be seen that treatment with the PSF could dose-dependently reduce the number of writhing episodes of mice in comparison with that of vehicle-treated animals, while rotundine, a positive analgesic agent, produced complete analgesia in this nociception model.

TABLE 8

| Groups | Dosages (mg/kg) | Writhing count | Inhibition (%) |
|---|---|---|---|
| Control | — | 15.60 ± 12.61 | |
| PSF | 200 | 1.63 ± 2.26** | 90 |
| PSF | 100 | 5.00 ± 6.65* | 68 |
| PSF | 50 | 10.25 ± 6.45 | 34 |
| Rotundine | 50 | 0.00 ± 0.00*** | 100 |

Each data represents the mean ± S.D. of 8–9 mice.
*** = $P < 0.001$;
** = $P < 0.01$;
* = $P < 0.05$, compared with the control group at the same time point.

III.4. Central Nociceptive Model Induced by Radiant Heat Stimulation in Mice.

III.4a. Method.

In still another embodiment, the present invention provides a method to determine the analgesic effect of the PSF comprising pubescenoside C and pubescenoside D, by examining the PSF with the tail flicking test involving radiant heat stimulation in mice.

The anti-nociceptive effects of PSF and the reference drug, expressed as the time required for mice tail flick after exposure to a source of radiant heat, were evaluated according to the description of d'Amour[3]. Briefly, animals were placed in a Plexiglas box that allowed their tails to be free, and then the box was placed on IITC model 336 tail flick analgesia meter (IITC Inc., USA) with the tail occluding a slit over a photocell for radiant heat stimulation generated by a power lamp mounted in a reflector. The tail-flick response was elicited by applying radiant heat to the point ⅓ of length away from the tip of the tail. The apparatus was arranged so that when the operator turned on the lamp a timer was activated. When the mice felt pain and flicked its tail, light fell on the photocell such that the timer was automatically stopped. The intensity of the heat stimulus in the tail-flick test was adjusted so that the animal flicked its tail within 3 to 6 seconds. A 12 seconds cut-off time was set in order to prevent tail tissues from damage. Before the experiment, the heat stimulation latency of all animals was tested, and those with response time to heat stimulation from 2 to 6 seconds were excluded. The tail-flick response was measured at 0.5, 1, and 2 hours after oral administration of PSF (200, 100 and 50 mg/kg body weight) or rotundine (50 mg/kg, as reference drug) or vehicle.

III.4b. Results and Analysis.

Figure 9:
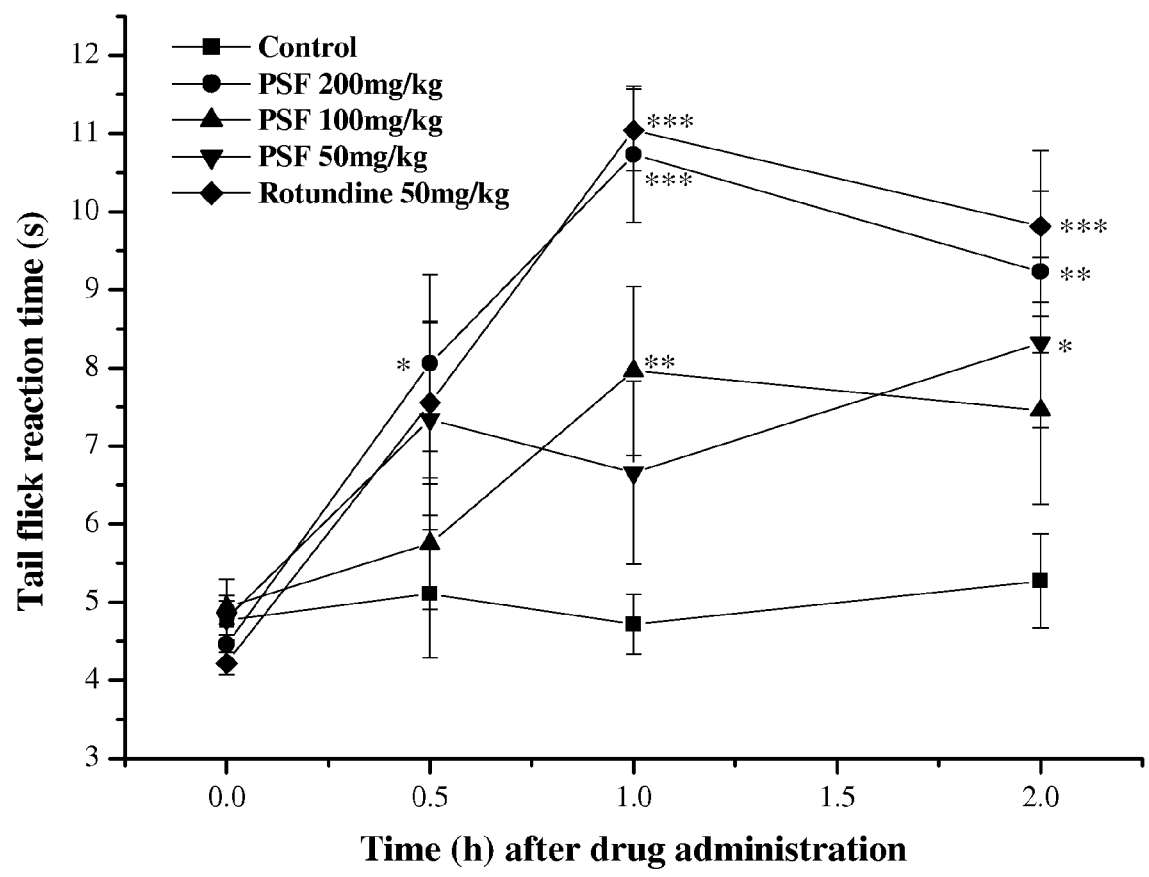
FIG. 9 shows the analgesic effect of PSF at different dosages on radiant heat stimulation-induced tail flick reaction of mice.

From the data illustrated in FIG. 9 and TABLE 9, it can be seen that treatment with the PSF could dose-dependently prolong the tail flick reaction time of mice in comparison with that of vehicle-treated animals. The reference drug rotundine prolonged the reaction time of the animals and demonstrated significantly anti-nociceptive action with a slightly stronger pharmacological intensity than that of the PSF.

TABLE 9

| Groups | Dosages (mg/kg) | Tail flick reaction time (s) | | | |
|---|---|---|---|---|---|
| | | 0 | 0.5 h | 1 h | 2 h |
| Control | — | 4.773 ± 0.781 | 5.106 ± 2.593 | 4.721 ± 1.195 | 5.271 ± 1.891 |
| PSF | 200 | 4.459 ± 0.843 | 8.061 ± 3.584* | 10.730 ± 2.737*** | 9.229 ± 3.268** |

TABLE 9-continued

| | Dosages | Tail flick reaction time (s) | | | |
|---|---|---|---|---|---|
| Groups | (mg/kg) | 0 | 0.5 h | 1 h | 2 h |
| PSF | 100 | 4.940 ± 1.047 | 5.748 ± 2.518 | 7.962 ± 3.228** | 7.458 ± 3.640 |
| PSF | 50 | 4.789 ± 0.861 | 7.339 ± 3.468 | 6.664 ± 3.310 | 8.319 ± 3.096* |
| Rotundine | 50 | 4.223 ± 0.458* | 7.552 ± 3.301 | 11.044 ± 1.658*** | 9.813 ± 3.069*** |

Each data represents the mean ± S.D. of 8-12 mice.
***= $P < 0.001$;
**= $P < 0.01$;
*= $P < 0.05$, compared with the control group at the same time point The preferred embodiments of the present invention are thus fully described. Although the description referred to particular embodiments, it will be clear to one skilled in the art that the present invention may be practiced with variation of these specific details. Hence, this invention should not be construed as limited to the embodiments set forth herein.

For example, a person skilled in the art will appreciate that other novel compounds, particularly other triterpene saponins, may be isolated by the method taught.

A person skilled in the art also will appreciate that a pharmaceutical composition comprising at least one of the novel triterpene saponins of the present invention may be readily prepared for use as an active compound for an anti-inflammatory and analgesic medication that may be administered orally or by injection.

The active fraction of the PSF may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like.

Such carriers include solid diluents or fillers, sterile aqueous media and various non-toxic organic solvents, etc. moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, PSF may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of PSF in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

The present invention may be used as a method to treat inflammation and pain in a mammalian subject, said method comprising the administrating to said subject the PSF in an amount sufficient to treat inflammation and pain.

The present invention may also be used in clinical practice with different dosage forms according to the above information. In addition, it is also possible to administer the PSFC topically and this may be done by way of creams, jellies, gels, pastes, patches, ointments and the like, in accordance with standard pharmaceutical practice.

For administration to animals other than humans, such as cattle or domestic animals, the PSF may be administered in the feed of the animals or orally as a drench composition.

The present invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Furthermore, the present invention may also be coupled with soluble polymers as targetable drug carriers. Such polymers can include polyvinylpyrrolidone, pyran copolymer, polyhydroxypropylmethacrylamide phenyl, polyhydroxyethyl-aspartamide-phenol, or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

REFERENCES

Articles of the scientific and patent literature cited herein are hereby incorporated in their entirety by reference by such citation.

[1] Winter C. A., Risley E. A., Nuss G. W., Proc. Soc. Exp. Bio. Med., 111, 544-547 (1962)

[2] Siegmund E., Cadmus R., Lu G., Proc. Soc. Exp. Bio. Med., 95. 729-731 (1957)

[3] D'Amour F. E., Smith D. L., J. Pharmacol. Exp. Ther., 72, 74-79 (1941)

What is claimed is:

1. A pharmaceutical composition comprising triterpene saponin component, said triterpene saponin component comprises
   a. 16% to 20% *Ilex*saponin B3;
   b. 1% to 4% pubescenoside D;
   c. 10% to 20% pubescenoside C;
   d. 18% to 28% *ilex*saponin B2;
   e. 20% to 42% chikusetsusaponin Iva;
   f. and 13% to 17% *ilex*saponin AI;
   wherein the total combined amount of said *ilex*saponin B3, said pubescenoside D, said pubescenoside C, said *ilex*saponin B2, said . . . chikusetsusaponin IVa, and said *ilex*saponin . . . A1 is at least 78% by proportion of said triterpene saponin component.

2. A pharmaceutical composition according to claim 1 wherein said triterpene saponin component is admixed in a pharmaceutically acceptable carrier, wherein said triterpene saponin having the following formula:

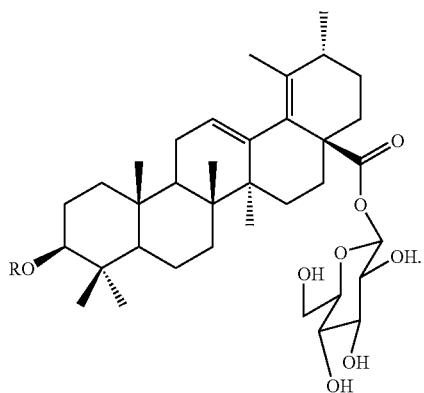

3. The pharmaceutical composition according to claim 2, wherein said triterpene saponin component is 1% to 100% of all the components in said pharmaceutical composition.

4. The pharmaceutical composition according to claim 2, wherein said R is Xyl$^2$-Glc, wherein said triterpene saponin is called pubescenoside C having the chemical structure:

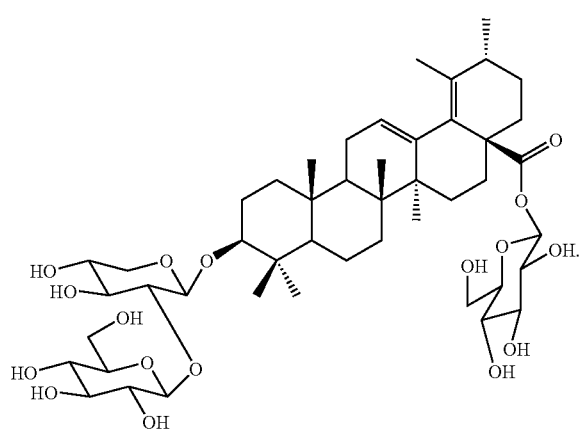

5. The pharmaceutical composition according to claim 4, wherein said pubescenoside C is 10% to 19% of said triterpene saponin component in said pharmaceutical composition.

6. The pharmaceutical composition according to claim 2, wherein said R is Xyl$^2$-Glc$^2$-Rha, wherein said triterpene saponin is called pubescenoside D

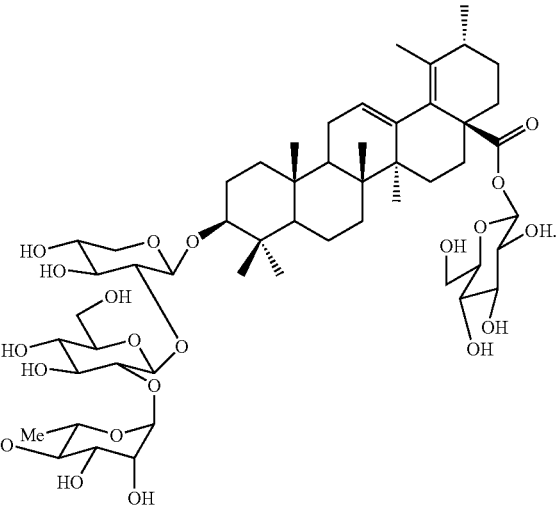

7. The pharmaceutical composition according to claim 6, wherein said pubescenoside D is 1% to 4% of said triterpenesaponin component in said pharmaceutical composition.

8. A method of obtaining said triterpene saponin component according to claim 1, comprising steps of:
   a. providing a plant material containing triterpene saponins;
   b. reducing the size of said plant material in step (a);
   c. extracting the size-reduced materials obtained in step (b) with methanol to obtain a methanol extract;
   d. extracting said methanol extract obtained in step (c) with butanol to obtain a butanol fraction;
   e. performing hydrophobic interaction chromatography on said butanol fraction obtained in step (d) by eluting with a methanol gradient of 0-100%; and
   f. analyzing each fractions obtained from said methanol gradient to positively identify the fractions containing the desired triterpene saponin.

9. The method according to claim 8 further comprising the steps of:
   g. pooling said positive fractions from step (f) to form a triterpene saponin fraction and further separating components in said triterpene saponin fraction over octadecyl silane (ODS) by eluting with a second methanol gradient of 50-100%;
   h. collecting fractions eluted at 70-100% methanol gradient from said step (g); and
   i. performing High Performance Thin Layer Chromatography (HPTLC) over silica gel on the fractions obtained in step (h) to identify the fraction containing the desired triterpene saponin.

10. The method according to claim 8, wherein said hydrophobic interaction chromatography of step (e) is performed using Diaion HP-20 resin.

11. The method according to claim 9, further comprising analyzing said triterpene saponin fraction by HPLC-ELSD, said HPLC-ELSD uses a mobile phase of CHCl3-MeOH—H20 with a step gradient of (9:1:0.1), (8:2:0.2) and (7:3:0.5).

12. The method according to claim 11, wherein said triterpene saponin fraction comprises
 a. 6% to 20% said *ilex*saponin B3;
 b. 1% to 4% said pubescenoside D;
 c. 10% to 19% said pubescenoside C;
 d. 18% to 28% said *ilex*saponin B2;
 e. 20% to 42% said chikusetsusaponin IVa, and;
 f. 13% to 17% said *ilex*saponin A1 by proportion of said triterpene saponin fraction.

* * * * *

UNITED STATES PATENT AND TRADEMARK OFFICE
CERTIFICATE OF CORRECTION

PATENT NO. : 7,544,668 B2  
APPLICATION NO. : 11/560849  
DATED : June 9, 2009  
INVENTOR(S) : Liang Liu et al.

Page 1 of 1

It is certified that error appears in the above-identified patent and that said Letters Patent is hereby corrected as shown below:

Column 15, line 7, claim 1 (c), the text "20%" should read --19%--; line 13, claim 1, the text "..." should be deleted; line 14, claim 1, the text "..." should be deleted.
Column 17, line 5, claim 12 (a), the text "6%" should read --16%--.

Signed and Sealed this

Thirteenth Day of April, 2010

David J. Kappos
*Director of the United States Patent and Trademark Office*